US 6,403,614 B1

(12) United States Patent
Dodge et al.

(10) Patent No.: US 6,403,614 B1
(45) Date of Patent: Jun. 11, 2002

(54) BENZOTHIOPHENES

(75) Inventors: Jeffrey Alan Dodge, Indianapolis, IN (US); Mark Gregory Stocksdale, Bloomsburg, PA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/164,024

(22) Filed: Sep. 30, 1998

Related U.S. Application Data

(60) Provisional application No. 60/060,944, filed on Oct. 3, 1997.

(51) Int. Cl.[7] ............... A61K 31/445; C07D 409/06; C07D 409/12
(52) U.S. Cl. ............ 514/324; 514/212; 514/255; 514/422; 514/443; 540/596; 546/202; 546/205; 548/525
(58) Field of Search .................. 514/212, 255, 514/324, 422, 443; 540/596; 546/202, 205; 548/525

(56) References Cited

U.S. PATENT DOCUMENTS

| | | | |
|---|---|---|---|
| 3,394,125 A | 7/1968 | Crenshaw | 548/525 |
| 3,413,305 A | 11/1968 | Crenshaw | 548/525 |
| 4,133,814 A | 1/1979 | Jones et al. | 546/202 |
| 4,230,862 A | 10/1980 | Suarez et al. | 546/237 |
| 4,358,593 A | 11/1982 | Jones et al. | 546/202 |
| 4,380,635 A | 4/1983 | Peters | 546/202 |
| 4,418,068 A | 11/1983 | Jones | 546/237 |
| 5,395,842 A | 3/1995 | Labrie | 514/320 |
| 5,470,854 A | 11/1995 | von Angerer et al. | 514/233 |
| 5,472,962 A | 12/1995 | Koizumi et al. | 514/233.5 |
| 5,484,795 A | 1/1996 | Bryant et al. | 514/319 |
| 6,271,227 B1 * | 8/2001 | Chirgadze et al. | 514/233.5 |

FOREIGN PATENT DOCUMENTS

| | | |
|---|---|---|
| EP | 062 503 | 10/1982 |
| WO | WO 89/02893 | 4/1989 |
| WO | WO 95/10513 | 4/1995 |

OTHER PUBLICATIONS

Crenshaw, R.R., et al., Potential Antifertility Agents, *J. Med. Chem.* vol. 14, No. 12, pp. 1185–1190 (1971).

Jones, C.D., et al., Antiestrogens, *J. Med. Chem.* vol. 27, pp. 1057–1066 (1984).

Jones, C.D., et al., Antiestrogens, *J. Med. Chem.* vol. 35 pp. 931–938 (1992).

* cited by examiner

Primary Examiner—Ceila Chang
(74) Attorney, Agent, or Firm—Gary M. Birch; Gilbert T. Voy

(57) ABSTRACT

This invention provides novel benzothiophene compounds of formula I:

which are useful for the inhibition of the various medical conditions associated with postmenopausal syndrome, as well as estrogen dependent diseases including cancer of the breast, uterus, and cervix. The present invention further. relates to pharmaceutical formulations of compounds of formula I.

17 Claims, No Drawings

BENZOTHIOPHENES

This application claims the benefit of U.S. Provisional Application No. 60/060,944 filed Oct. 3, 1997.

FIELD OF INVENTION

This invention relates to the fields of pharmaceutical and organic chemistry and provides novel benzothiophene compounds which are useful for the inhibition of the various medical conditions associated with postmenopausal syndrome, as well as estrogen-dependent diseases including cancer of the breast, uterus, and cervix.

BACKGROUND OF THE INVENTION

"Postmenopausal syndrome" is a term used to describe various pathological conditions which frequently affect women who have entered into or completed the physiological metamorphosis known as menopause. Although numerous pathologies are contemplated by the use of this term, three major medical conditions of postmenopausal syndrome are the source of the greatest long-term medical concern: osteoporosis, cardiovascular effects such as hyperlipidemia, and estrogen-dependent cancer such as breast and uterine cancer.

Osteoporosis, which generally includes a group of disorders which arise from diverse etiologies, is characterized by the net loss of bone mass per unit volume. The consequence of this loss of bone mass and resulting bone fracture is the failure of the skeleton to provide adequate structural support for the body. One of the most common types of osteoporosis is that associated with menopause. Most women lose from about 20% to about 60% of the bone mass in the trabecular compartment of the bone within three to six years after the cessation of menses. This rapid loss is generally associated with an increase of bone resorption and formation. However, the resorptive cycle is more dominant and the result is a net loss of bone mass.

Osteoporosis is a common and serious disease among postmenopausal women. There are an estimated 25 million women in the United States who are afflicted with this disease. The results of osteoporosis disease's sequelae are personally harmful and often result in the need for extensive and long term medical support (hospitalization and nursing home care). This is especially true in elderly patients. Additionally, although osteoporosis is not generally thought of as a life threatening condition, a 20% to 30% mortality rate is related with hip fractures in elderly women. A large percentage of this mortality rate can be directly associated with postmenopausal osteoporosis.

The trabecular tissue is the most vulnerable bone tissue to the effects of postmenopausal osteoporosis. This tissue is often referred to as spongy or cancellous bone and is particularly concentrated near the ends of the bone (near the joints) and in the vertebrae of the spine. The trabecular tissue is characterized by small osteoid structures which interconnect with each other, as well as the more solid and dense cortical tissue which makes up the outer surface and central shaft of the bone. This interconnected network of trabeculae gives lateral support to the outer cortical structure and is critical to the biomechanical strength of the overall structure. In postmenopausal osteoporosis, it is loss of the trabeculae which leads to the failure and fracture of bone. In light of the loss of the trabeculae in postmenopausal women, it is not surprising that the most common fractures are those associated with bones which are highly dependent on trabecular support, e.g., the vertebrae and the neck of the weight bearing bones, such as the femur and the fore-arm. Indeed, hip fracture, collies fractures, and vertebral crush fractures are hallmarks of postmenopausal osteoporosis.

At this time, the generally accepted method for treatment of postmenopausal osteoporosis is estrogen replacement therapy (ERT). Although ERT is generally successful, patient compliance with this therapy is low primarily because estrogen treatment frequently produces undesirable side effects.

Prior to menopause, most women have less incidence of cardiovascular disease than age-matched men. Following menopause, however, the rate of cardiovascular disease in women, such as hyperlipidemia, increases to match the rate seen in men. This rapid increase in the incidence of cardiovascular disease has been linked, in part, to the loss of estrogen and to the loss of estrogen's ability to regulate serum lipids. The nature of estrogen's ability to regulate serum lipids is not well understood, but evidence to date indicates that estrogen can upregulate the low density lipid (LDL) receptors in the liver to remove excess cholesterol. Additionally, estrogen appears to have some effect on the biosynthesis of cholesterol, as well as other beneficial effects on cardiovascular health.

It has been reported in the literature that postmenopausal women undergoing estrogen replacement therapy have a return of serum lipid levels to concentrations similar to those of the premenopausal state. Thus, estrogen would appear to be a reasonable treatment for this condition. However, the side-effects of ERT are not acceptable to many women, thus limiting the use of this therapy. An ideal therapy for this condition would be an agent which would regulate the serum lipid levels like estrogen, but would be devoid of the side-effects and risks associated with estrogen therapy.

The third major pathology associated with postmenopausal syndrome is estrogen-dependent cancer, primarily breast and uterine cancer. Although such neoplasms are not solely limited to postmenopausal women, they are more prevalent in the older postmenopausal population. Current chemotherapy of these cancers has relied heavily on the use of estrogen agonist/antagonist compounds, such as tamoxifen. Although such mixed agonist/antagonists have beneficial effects in the treatment of these cancers, the estrogenic side-effects are tolerable in only acute life-threatening situations. These agents have stimulatory effects on certain cancer cell populations in the uterus due to their estrogenic (agonist) properties and therefore, arecontraproductive in some cases. A better therapy for the treatment of these cancers would be an agent which is an antiestrogenic compound in cancerous tissue, having negligible or no estrogen agonist properties on other reproductive tissues.

In response to the clear need for new pharmaceutical agents which are capable of alleviating the symptoms of, inter alia, postmenopausal syndrome, the present invention provides new compounds, pharmaceutical compositions thereof, and methods of using such compounds for the inhibition of postmenopausal syndrome and other estrogen-related pathological conditions such as those mentioned herein.

SUMMARY OF THE INVENTION

The present invention relates to compounds of formula

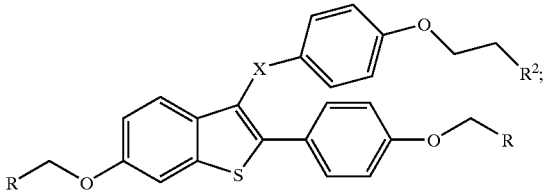

I wherein:

R is independently at each occurrence NHC(O)R$^1$, OR$^1$, or SR$^1$;

R$^1$ is C$_1$–C$_6$ alkyl or aryl;

R$^2$ is pyrrolidin-1-yl, pipiperidin-1-yl, or hexamethyleneimin-1-yl; and

X is C=O, CH—OH, CH$_2$, O, or S; or a pharmaceutically acceptable salt or solvate thereof.

The present invention further relates to pharmaceutical formulations containing compounds of formula I and the use of such compounds for alleviating the symptoms of post-menopausal syndrome, particularly osteoporosis, cardiovascular-related pathological conditions, and estrogen-dependent cancer.

DETAILED DESCRIPTION OF THE INVENTION

As used herein, the term "C$_1$–C$_4$ alkyl" represents a methyl, ethyl, propyl, isopropyl, cyclopropyl, butyl, cyclobutyl, s-butyl, or a t-butyl group. The term "C$_1$–C$_6$ alkyl" includes "C$_1$–C$_4$ alkyl" groups in addition to straight, branched or cyclic alkyl groups having five or six carbon atoms and also includes, but is not limited to, pentyl, isopentyl, hexyl, 2-methylpentyl, cyclopentyl, cyclohexyl, and like groups.

The term "aryl" represents phenyl, benzyl, substituted phenyl, and substituted benzyl groups.

The terms "substituted phenyl" and "substituted benzyl" represent a phenyl and benzyl group substituted with one to five moieties chosen from the group consisting of halo, hydroxy, nitro, C$_1$–C$_4$ alkyl, C$_1$–C$_4$ alkoxy, trichloromethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 2,4-dinitrophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6,difluorophenyl, 2,6-dimethylphenyl, 2-fluoro-5-methylphenyl, 2,4,6-trifluorophenyl, 2-trifluoromethylphenyl, 2-chloro-5-trifluoromethylphenyl, 3,5-bis-(trifluoromethyl)phenyl, 2-methoxyphenyl, 3-methoxyphenyl, 3,5-dimethoxyphenyl, 2-methyl-4-nitrophenyl, 4-methoxy-2-nitrophenyl, and the like. Examples of a substituted benzyl group would include all the compounds named when the word "benzyl" is substituted for the word "phenyl" in all the previously mentioned examples of a substituted phenyl group.

The term "hydroxy protecting group" denotes a group understood by one skilled in the organic chemical arts of the type described in Chapter 2 of "Protective Groups in Organic Synthesis, 2nd Edition, T. H. Greene, et al., John Wiley & Sons, New York, 1991, hereafter *"Greene"*.

The term "phase transfer catalyst" refers to a salt in which the cation has large nonpolar substituent groups which confer good solubility on the salt in organic solvents. The most common examples are tetraalkylammonium and tetraalkylphosphonium ions e.g. tetraalkylammonium chloride or bromide or (C$_8$–C$_{10}$ trialkyl)methylammonium chloride (Adogen® 464).

Although the free-base form of formula I compounds can be used in the methods of the present invention, it is preferred to prepare and use a pharmaceutical salt form. Typical pharmaceutical salts include those salts prepared by reaction of the compounds of the present invention with a mineral or organic acid. Such salts are known as acid addition salts. Thus, the term "pharmaceutical salt" refers to acid addition salts of a compound of formula I which are substantially non-toxic at the doses administered and are commonly known in the pharmaceutical literature. See e.g. Berge, S. M, Bighley, L. D., and Monkhouse, D. C., *J. Pharm. Sci.*, 66, 1, 1977.

Examples of such pharmaceutically acceptable salts are the iodide, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, naphthalene-2-benzoate, bromide, isobutyrate, phenylbutyrate, g-hydroxybutyrate, b-hydroxybutyrate, butyne-1,4-dioate, hexyne-1,4-dioate, hexyne-1,6-dioate, caproate, caprylate, chloride, cinnamate, citrate, decanoate, formate, fumarate, glycollate, heptanoate, hippurate, lactate, malate, maleate, hydroxymaleate, malonate, mandelate, mesylate, nicotinate, isonicotinate, nitrate, oxalate, phthalate, terephthalate, phosphate, monohydrogenphosphate, dihydrogenphosphate, metaphosphate, pyrophosphate, propiolate, propionate, phenylpropionate, salicylate, sebacate, succinate, suberate, sulfate, bisulfate, pyrosulfate, sulfite, bisulfite, sulfonate, benzenesulfonate, p-bromophenylsulfonate, chlorobenzenesulfonate, propanesulfonate, ethanesulfonate, 2-hydroxyethanesulfonate, methanesulfonate, naphthalene-1-sulfonate, naphthalene-2-sulfonate, p-toluenesulfonate, xylenesulfonate, tartarate, and the like of a compound of formula I.

By "pharmaceutical formulation" it is meant that in a formulation containing the compound of formula I, the carrier, diluent, excipients, and salt must be compatible with the other ingredients of the formulation, and not deleterious to the recipient thereof.

The term "solvate" represents an aggregate that comprises one or more molecules of the solute, such as a formula I compound, with one or more molecules of solvent.

As used herein, the term "effective amount" means an amount of compound of the present invention which is capable of inhibiting the symptoms of the various pathological conditions herein described.

The terms "inhibit" or "inhibiting" bear their usual meaning which includes prohibiting, treating, alleviating, ameliorating, halting, restraining, slowing or reversing the progression, or reducing the severity of a pathological symptom related to or resultant from post menopausal syndrome. As such, these methods include both medical therapeutic (acute) and/or prophylactic (prevention) administration as appropriate.

While all of the compounds of the present invention are useful, certain of the compounds are particularly interesting and are preferred. The following listing sets out several groups of preferred compounds. It will be understood that each of the listings may be combined with other listings to create additional groups of preferred compounds.

aa) X is C=O;
ab) X is O;
ac) R at each occurrence is $SR^1$;
ad) R at each occurrence is S-($C_1$-$C_4$ alkyl);
ae) R at each occurrence is S-phenyl;
af) R at each occurrence is $OR^1$;
ag) R at each occurrence is O-($C_1$-$C_4$ alkyl);
ah) R at each occurrence is NHC(O)-$R^1$;
ai) R at each occurrence is NHC(O)-phenyl;
aj) $R^2$ is piperidin-1-yl;
ak) the compound of formula I is a salt; and
al) the compound of formula I is the hydrochloride salt.

Specific preparations of compounds of the present invention are described herein, in Examples 1–5. Modification to the methods described below may be necessary to accommodate reactive functionalities of particular substituents. Such modification would be both apparent to, and readily ascertained by, those skilled in the art. The following schemes generally illustrate the preparation of compounds of formula I.

The compounds of formula I where R at each occurrence is the same may be prepared from compounds of formula II as illustrated in Scheme 1 below where X' is C=O, O, or S, Y is halo or hydroxy, and R and $R^2$ are as described supra.

Scheme 1

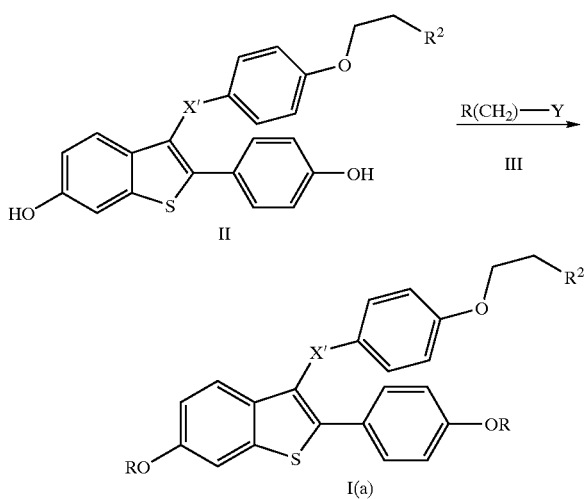

When Y is halo, compounds of formula I(a) may be prepared by dissolving or suspending a compound of formula II in a suitable organic solvent, in the presence of a suitable base, and adding a compound of formula III. The presence of a phase transfer catalyst is also an optional reagent depending on the solvent system and base as discussed below. Additionally, when Y is chloro, sodium iodide may also be employed to aid in the displacement reaction. Once all the ingredients are combined, the reaction is allowed to proceed at temperatures ranging from 0° C. to the reflux temperature of the reaction mixture. Typically the reaction is performed at ambient temperatures. The reaction time will depend upon the compound of formula III. When R is $OR^1$ or NHC(O)$R^1$l, reaction times generally will range from about 20 minutes to 2 hours. When R is $SR^1$ however, reaction times tend to be longer and range from about 8 to 24 hours. A reaction time of about 18 hours is typical.

Suitable organic solvents include, but are not limited to, N,N-dimethylpropyleneurea (DMPU), methylene chloride, tetrahydrofuran, chloroform, ethyl acetate, acetonitrile, mixtures thereof, and the like. DMPU and methylene chloride individually are typically preferred solvents. Suitable bases include but are not limited to metal hydrides and metal hydroxides, e.g. sodium, potassium, or lithium hydride and hydroxide. Sodium hydride and aqueous sodium hydroxide individually are typically preferred bases. When aqueous sodium hydroxide is employed the reaction is preferably run in the presence of a phase transfer catalyst. Adogen® 464 is a preferred phase transfer catalyst.

The compound of formula III is typically employed in a stoichiometric excess. For example, when R is $SR^1$, from 2 to about 2.5 equivalents, relative to the compound of formula II, is generally employed, while 2.3 equivalents is typically preferred. When R is $OR^1$ or NHC(O)$R^1$, from 9.5 to 10.5 equivalents are preferably employed while 10.0 equivalents are typically preferred. The base is also generally employed in a molar excess. For example, from 3.5 to about 6.5 equivalents are typically employed. When aqueous sodium hydroxide is employed, a preferred amount is about 5.8 to about 6.2 equivalents. When sodium hydride is employed, a preferred amount is about 3.8 to about 4.2 equivalents. The phase transfer catalyst, when used, is employed in a stoichiometric deficiency. Typically, about 0.05 to 0.15 equivalents, relative to the compound of formula II is employed. A preferred amount is about 0.10 equivalents.

Compounds of formula I(a) may also be prepared by the Mitsunobo reaction of a compound of formula II with a compound of formula III where Y is hydroxy. This transformation is accomplished by dissolving or suspending a compound of formula II in a suitable solvent and adding a suitable base, a compound of formula III where Y is hydroxy, triphenyl phosphine, and diethylazodicarboxylate. The resulting mixture is allowed to stir for from 2 to 24 hours at ambient temperature, but the reaction is typically complete in from 16 to 20 hours. The reaction is preferably allowed to run for about 18 hours. Suitable solvents include anhydrous solvents, such as methylene chloride, acetonitrile, chloroform, ethyl acetate, mixtures thereof, and the like. Typically, anhydrous tetrahydrofuran is a convenient and preferred solvent. Suitable bases include, but are not limited to, carbonates, bicarbonates, and hydroxides (e.g. lithium, sodium, or potassium carbonate, bicarbonate, or hydroxide), tri-($C_1$-$C_4$ alkyl)amines (e.g. triethylamine), or aromatic nitrogen containing heterocycles (e.g. pyridine). Triethylamine is a preferred base.

The base is preferably employed in a stoichiometric amount relative to the compound of formula II, but excesses on the order of 0.01 to 0.1 equivalents are acceptable. The compound of formula III, triphenyl phosphine, and diethylazodicarboxylate are typically employed in a molar excess relative to the compound of formula II. The compound of formula III is typically employed in about a 2 to 3 molar excess, while a 2.5 molar excess is a preferred amount. The triphenyl phosphine and diethylazodicarboxylate are usually employed in about a 3.5 to about a 4.5 molar excess while a 4.0 molar excess is typically preferred. For further instruction on conditions and reagents useful in the Mitsunobo reaction see Mitsunobo's review article in *Synthesis*, 1, (1981).

The compounds of formula I where R at each occurrence is not the same may be prepared from compounds of formula IV or V as illustrated in Scheme 2 below where Pg is a hydroxy protecting group, $R^3$ has the same scope as R but R and $R^3$ are different within the same molecule, and R, $R^2$, X', and Y are as described supra.

The hydroxy protecting groups in compounds of formula VI and VII may be removed by well known methods in the art. Numerous reactions for the formation and removal of hydroxy protecting groups are described in a number of

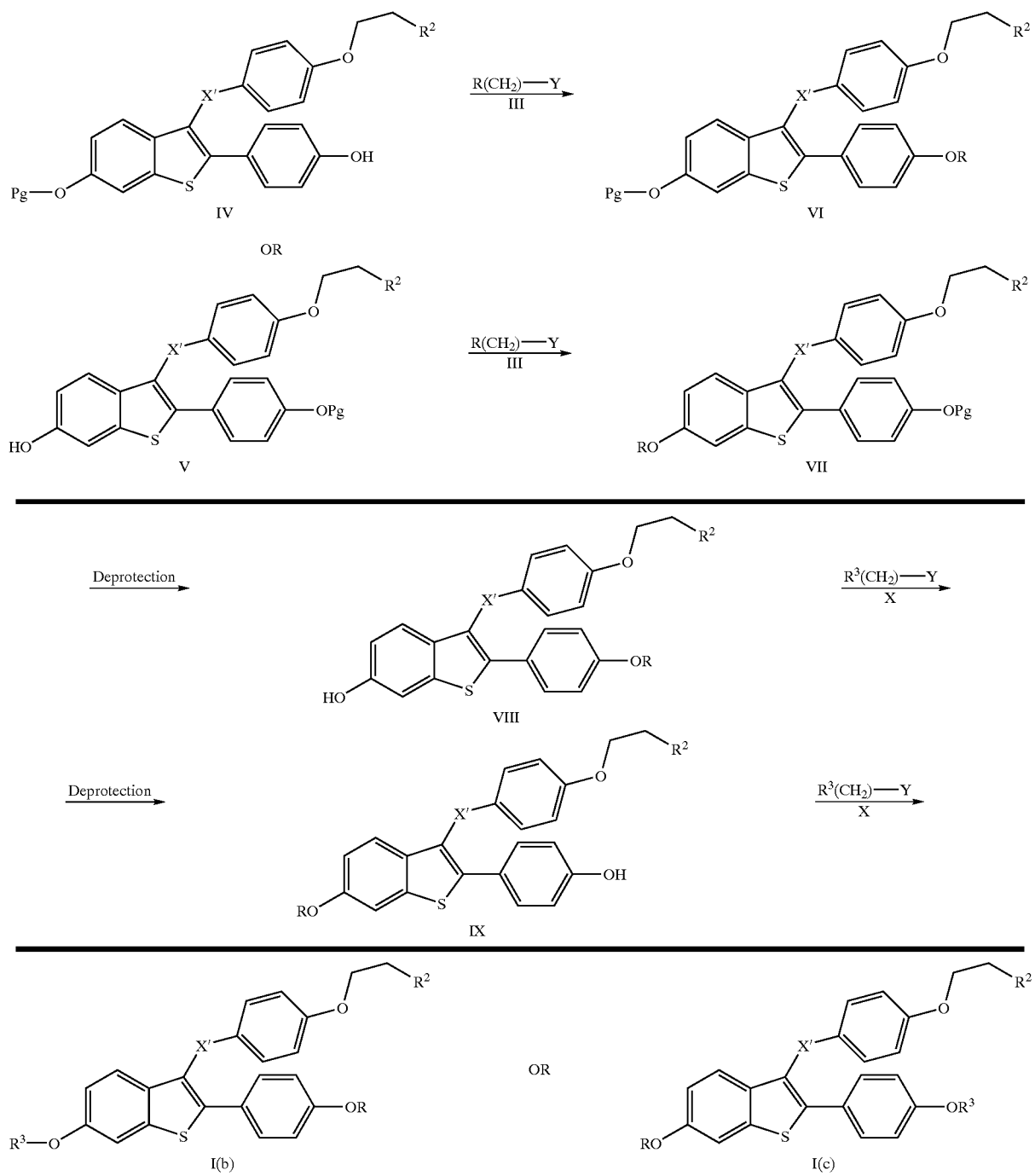

The coupling of a compound of formula III to a compound of formula IV or V may be performed as described above in Scheme 1. Similarly, a compound of formula X may also be coupled to a compound of formula VIII or IX as described above in Scheme 1.

standard works including, for example, *The Peptides*, Vol. I, Schrooder and Lubke, Academic Press (London and New York, 1965), (hereafter referred to as *The Peptides*) and *Greene.*

The compounds of formula I where X is CH—OH or $CH_2$ may be prepared from compounds of formula I where X is C=O essentially as described in U.S. Pat. No. 5,484,798, the teachings of which are hereby incorporated by reference.

The pharmaceutical acid addition salts are typically formed by reacting a compound of formula I in its free base form with an equimolar or excess amount of acid. The reactants are generally combined in a polar organic solvent such as methanol or ethyl acetate. The salt normally precipitates out of solution within about one hour to 10 days and can be isolated by filtration, or the solvent can be stripped off by conventional means.

The pharmaceutical salts generally have enhanced solubility characteristics compared to the compound from which they are derived, and thus are often more amenable to use in pharmaceutical formulations.

Compounds of formula II are well known in the art and may be prepared as described in U.S. Pat. No. 4,358,593 the teachings of which are hereby incorporated by reference. Compounds of formula III and X are also well known in the art and are generally commercially available. Compounds of formula III and X where R or $R^3$ is NHC(O)$R^1$ and Y is hydroxy may also be prepared as described in *J.Org.Chem.*, 57, 1702, (1992).

The compounds of formula IV and V may be prepared from bis-hydroxy protected compounds of formula XI:

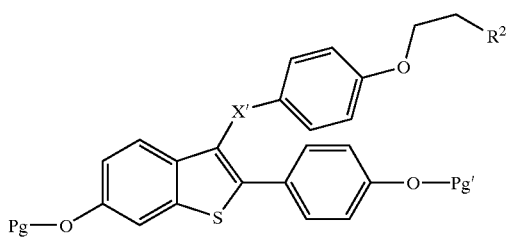

XI where Pg and Pg' are different hydroxy protecting groups, by selectively removing one of the hydroxy protecting groups leaving the other intact. Choices of hydroxy protecting groups which facilitate a selective removal and methods for the selective removal of one hydroxy protecting group over the other are well known in the art given the guidance of *Greene* and *The Peptides*. One example where selective removal is possible is where one protecting group is benzyl and the other is a $C_1-C_4$ alkyl group. The benzyl group may be removed selectively by catalytic hydrogenation. In general, preferred protecting groups are benzyl and $C_1-C_4$ alkyl groups and especially preferred are methyl and isopropyl groups.

Methods of preparing differentially protected compounds of formula XI are known in the art. One method, where X is C=O, may be found in U.S. Pat. No. 5,420,349, the teachings of which are hereby incorporated by reference. Compounds of formula XI where X is O may be prepared as taught in U.S. Pat. No. 5,723,474 the teachings of which are hereby incorporated by reference. Compounds of formula XI where X is S may be prepared essentially as described for compounds of formula XI where X is O.

The optimal time for performing the reactions of Schemes 1–2 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. Intermediate and final products may be purified, if desired by common techniques such as recrystallization or chromatography over solid supports such as silica gel or alumina.

The synthetic steps of the routes described herein may be combined in other ways to prepare the formula I compounds. The discussion of the synthesis is not intended to be limiting to the scope of the present invention, and should not be so construed. Application of the above chemistry enables the synthesis of the compounds of formula I, which would include, but not be limited to:

1) [6-ethylthiomethoxy-2-(4-[ethylthiomethoxy]phenyl)benzo[b]thiophen-3-yl][4-([2-piperidin-1-yl]ethoxy)phenyl]methanol;
2) [6-phenoxymethoxy-2-(4-phenxoxymethoxyphenyl)benzo[b]thiophen-3-yl][4-([2-pyrrolidin-1-yl]ethoxy)phenyl]sulfide;
3) [6-butoxymethoxy-2-(4-butoxyphenoxyphenyl)benzo[b]thiophen-3-yl][4-([2-hexamethyleneimin-1-yl]ethoxy)phenyl]ether;
4) [6-isopropylthiomethoxy-2-(4-[isopropylthiomethoxy]phenyl)benzo[b]thiophen-3-yl][4-([2-piperidin-1-yl]ethbxy)phenyl]methane;
5) [6-Acetamidylmethoxy-2-(4-Acetamidylmethoxyphenyl)benzo[b]thiophen-3-yl][4-([2-pyrrolidin-1-yl]ethoxy)phenyl]methanol; and
6) [6-Propionamidylmethoxy-2-(4-Propionamidylmethoxyphenyl)benzo[b]thiophen-3-yl][4-([2-hexamethyleneimin-1-yl]ethoxy)phenyl]sulfide.

The following Preparations and Examples further illustrate the synthesis of the compounds of the present invention. The examples are not intended to be limiting to the scope of the invention in any respect, and should not be so construed. All experiments were run under positive pressure of dry nitrogen. The terms and abbreviations used in the instant preparations and examples have their normal meanings unless otherwise designated. For example "° C.", "N", "mmol", "g", "L", "M", "HPLC", "EA", "IR", and "$^1$H-NMR", refer to degrees Celsius, normal or normality, millimole or millimoles, gram or grams, milliliter or milliliters, molar or molarity, high performance liquid chromatography, elemental analysis, infrared, and proton nuclear magnetic resonance respectively.

PREPARATIONS

Preparation 1

N-Hydroxymethylbenzamide

Benzamide (25 g, 206 mmol), formaldehyde (37% aqueous, 70 mL, 890 mmol), and potassium carbonate (700 mg, 5 mmol) were mixed in 36 mL of water. The mixture was heated at 45° C. long enough to dissolve the reagents and then cooled to room temperature. The reaction was allowed to proceed for 48 hours when $^1$H NMR indicated that the reaction was complete. The reaction was diluted with about 500 mL of water and crystals began to form and were allowed to continue to form for 18 hours. The crystals were collected by vacuum filtration, washed with water, and vacuum dried at 40° C. The filtrate was extracted with ethyl acetate and the organic layer was dried over sodium sulfate, filtered, and evaporated to give a white solid which was also vacuum dried at 40°C. The lots were combined for a total of 29.0 g of title compound. 93%. $^1$H NMR consistent with title compound.

EXAMPLES

Example 1

2-(4-[Methylthiomethoxy]phenyl)-3-(4-[(2-Piperidin-1-yl)ethoxy]benzoyl)-6-Methylthiomethoxybenzo[b]thiophene Hydrochloride Salt To 2-(4-hydoxyphenyl)-3-(4-[2-piperidinyl]ethoxybenzoyl-6-hydroxybenzo[b]thiophene (2.0 g, 3.93 mmol) stirring in N,N-dimethylpropyleneurea (50 ml) at room temperature was added sodium hydride (0.63 g, 15.7 mmol). After 1 hour, chloromethyl methyl sulfide (0.88 g, 9.02 mmol) was then added to the dark red solution and the reaction stirred at room temperature overnight. Ethyl acetate was added and this mixture was washed with brine, water, dried over sodium sulfate, filtered, and evaporated to give a yellow oil. The oil was purified by flash chromatography (silica gel, ethyl acetate). The isolated product was taken up in tetrahydrofuran and 1 equivalent of 1N aqueous hydrochloric acid was added. The solution was evaporated immediately then concentrated to give 1.5 g (61%) of the title product. $^1$H-NMR (300 MHz, DMSO-$d_6$) δ 10.72–11.25 (br. s, 1H), 7.76–7.77 (d, 1H, J=2.2 Hz), 7.72–7.75 (d, 2H, J=8.5 Hz), 7.34–7.36 (d, 3H, J=8.7 Hz), 7.05–7.09 (dd, 1H, J=8.8 Hz; J=2.2 Hz), 6.97–7.01 (dd, 4H, J=8.7 Hz; J=3.4 Hz), 5.37 (s, 2H), 5.25 (s, 2H), 4.24–4.44 (br. s, 2H), 2.57–3.51 (br. s, 6H), 2.21 (s, 3H), 2.14 (s, 3H), 1.31–1.83 (m, 5H), 1.36 (s, 1H). MS (FD) 593 (M$^+$-HCl);

Example 2

2-(4-[Phenylthiomethoxy]phenyl)-3-(4-[(2-Piperidin-1-yl)ethoxy]benzoyl)-6-Phenylthiomethoxybenzo[b]thiophene Hydrochloride Salt To 2-(4-hydoxyphenyl)-3-(4-[2-piperidinyl] ethoxybenzoyl-6-hydroxybenzo[b]thiophene (2.0 g, 3.92 mmol) stirring in N,N-dimethylpropyleneurea (40 ml) at room temperature was added sodium hydride (0.63 g, 15.7 mmol). After 1 hour, chloromethyl phenyl sulfide (1.43 g, 9.02 mmol) was then added to the dark red solution followed by sodium iodide (1.35 g, 9.02 mmol). The reaction was allowed to stir at room temperature overnight then diluted with ethyl acetate and brine. The organic extract was washed with brine, water, dried over sodium sulfate, filtered and concentrated to an oil. The resulting oil was purified by flash chromatography (silica gel, ethyl acetate). The free base was taken up in acetonitrile/tetrahydrofuran followed by addition of 1.0N aqueous hydrochloric acid (2.0 ml). The solution was concentrated immediately to give 1.45 g (49%) of a the title compound. MS (FD) 717 (M$^+$-HCl); Anal. calcd. for $C_{42}H_{40}NO_4S_3Cl$: C, 66.87; H, 5.34; N, 1.86; Found: C, 67.12; H, 5.42; N, 1.77.

Example 3

2-(4-[Ethoxymethoxy]phenyl)-3-(4-[(2-Piperidin-1-yl)ethoxy]benzoyl)-6-Ethoxymethoxybenzo[b]thiophene Hydrochloride Salt To 2-(4-hydoxyphenyl)-3-(4-[2-piperidinyl] ethoxybenzoyl-6-hydroxybenzo[b]thiophene (2.0 g, 3.92 mmol) stirring in anhydrous methylene chloride (50 ml) at room temperature was added 1N aqueous sodium hydroxide (24 ml, 24 mmol). After 5 min, Adogen® 464 (0.18 g, 0.39 mmol) was added followed by chloromethyl ethyl ether (3.67 g, 39 mmol). After 10 min, sodium hydroxide (excess of a 1N aqueous solution) was added and the resulting mixture stirred for 10 minutes then extracted with methylene chloride. The combined organic extracts were washed with brine, dried over sodium sulfate, filtered, and concentrated to give a yellow oil which was purified by flash chromatograpy (silica gel, ethyl acetate). The isolated product was then taken up in tetrahydrofuran and hydrochloric acid (2 mL of a 1N aqueous solution) subsequently added. The solution was concentrated to give 1.7 g (69%) of the title compound. MS (FD) 589 (M$^+$-HCl); Anal. calcd. for $C_{34}H_{40}NO_6SCl$: C, 65.21; H, 6.44; N, 2.24; Found: C, 65.41; H, 6.61; N, 2.18.

Example 4

2-(4-[Methoxymethoxy]phenyl)-3-(4-[(2-Piperidin-1-yl)ethoxy]benzoyl)-6-Methoxymethoxybenzo[b]thiophene Hydrochloride Salt To 2-(4-hydoxyphenyl)-3-(4-[2-piperidinyl] ethoxybenzoyl-6-hydroxybenzo[b]thiophene (2.0 g, 3.92 mmol) stirring in anhydrous methylene chloride (50 ml) at room temperature was added sodium hydroxide (24 ml of a 1 N aqueous solution, 24 mmol). The solution was stirred for 5 minutes and Adogen® 464 (0.18 g, 0.39 mmol) was then added. After 10 minutes, chloromethyl methyl ether (3.18 g, 39 mmol) was then added slowly. After 10 min, the reaction mixture was diluted with water, then extracted with methylene chloride. The combined organic extracts were dried over sodium sulfate, filtered, and concentrated to give a yellow oil which was purified by flash chromatograpy (silica gel, ethyl acetate). The isolated product was then taken up in acetonitrile (20 ml) followed by addition of hydrochloric acid (1 eq of a 1N ethereal solution). The solution was immediately evaporated to give 1.36 g (58%) of the title compound. $^1$H NMR (300 MHz, DMSO-$d_6$) δ 10.89–11.14 (m, 1H), 7.68–7.78 (m, 3H), 7.32–7.39 (m, 3H), 7.08–7.12 (dd, 1H, J=8.8; J=2.2 Hz), 6.95–7.04 (m, 4H), 5.28 (s, 2H), 5.18 (s, 2H), 4.43–4.46 (t, 2H), 3.39–3.53 (m, 4H), 3.43 (s, 3H), 3.35 (s, 3H), 2.90–2.99 (app. q, 2H), 1.62–1.92 (m, 5H), 1.28–1.44 (m, 1H). MS (FD) 561 (M$^+$-HCl).

Example 5

2-(4-[Benzamidylmethoxy]phenyl)-3-(4-[(2-Piperidin-1-yl)ethoxy]benzoyl)-6-Benzamidylmethoxybenzo[b]thiophene To 2-(4-hydoxyphenyl)-3-(4-[2-piperidinyl] ethoxybenzoyl-6-hydroxybenzo[b]thiophene (2.0 g, 3.92 mmol), triethylamine (0.40 g, 3.92 mmol), N-hydroxymethylbenzamide (1.48 g, 9.8 mmol), and triphenylphosphine (4.11 g, 15.7 mmol) stirring in tetrahydrofuran (50 mL) at −3° C. was added via dropping funnel diethyl azidodicarboxylate (2.73 g, 15.7 mmol) in tetrahydrofuran (20 ml) at such a rate the reaction temperature was maintained below 0° C. The reaction was then allowed to warm to room temperature and to stir overnight. The solvent was evaporated to give a yellow oil which was purified by flash chromatography (silica gel, 0–15% methanol/ethyl acetate) to give 1.0 g (34%) of the title compound. MS (FD) 740 (M+); Anal. calcd. for $C_{44}H_{41}N_3O_6S$: C, 71.43; H, 5.59; N, 5.68; Found: C, 71.59; H, 5.72; N, 5.44.

Representative compounds of the present invention have been biologically tested to demonstrate their efficacy for inhibiting the effects of post menopausal syndrome.

Estrogenicity: Four Day Ovariectomized Rat Model
General Preparation Procedure

Seventy-five day old female Sprague Dawley rats (weight range of 225 g–275 g) were obtained from Charles River Laboratories (Portage, Mich.). The animals were either bilaterally ovariectomized (OVX) or exposed to a Sham surgical procedure at Charles River Laboratories, and then shipped after one week. Upon arrival, these rats were housed in metal hanging cases in groups of three or four animals per cage, and had ad libitum access to food (Teklad diet, TD 89222, 0.5% calcium, 0.4% phosphorous; Madison, Wis.) and water. Room temperature was maintained at 22.2° C.±1.7° C. with a minimum relative humidity of 40%. The photoperiod in the room was twelve hours light and twelve hours dark. Comparative data were obtained between untreated ovariectomized rats, ovariectomized rats treated with 17α-ethynylestradiol ($EE_2$), and ovariectomized rats treated with representative compounds of the present invention.

Dosing Regimen/Tissue Collection

After a one-week acclimation period (two weeks post-OVX), daily dosing with test compound and 17α-ethynylestradiol was initiated. The test compounds or 17α-ethynylestradiol (Sigma Chemical Co., St. Louis, Mo.) were given orally, unless otherwise stated, as a suspension in 20% cyclodextrin (CDX). 20% CDX was used as the control vehichle. Animals were dosed daily for four days. Following the dosing regimen, animals were weighed and anesthetized with a ketamine:xylazine (2:1, v:v) mixture and a blood sample was collected by cardiac puncture. The animals were then sacrificed by asphyxiation with $CO_2$, the uterus was removed through a midline incision, and a wet uterine weight was determined.

Serum Cholesterol Analysis

The blood samples, collected as described above, were allowed to clot at room temperature for two hours, and serum was obtained following centrifugation for ten minutes at 3000 rpm. Serum cholesterol was determined using a high-performance cholesterol assay (Boehringer Mannheim Diagnostics, Indianapolis, Ind.). Briefly, the cholesterol was oxidized to produce cholest-4-en-3-one and hydrogen peroxide. The hydrogen peroxide was then reacted with phenol and 4-aminophenazone in the presence of peroxidase to produce a p-quinoneimine dye, which was read spectrophotometrically at 500 nm. Cholesterol concentration was then calculated against a standard curve.

Uterine Eosinophil Peroxidase (EPO) Assay

Uteri were kept at 4° C. until time of enzymatic analysis. The uteri were then homogenized in 50 volumes of 50 nM Tris buffer (pH=8.0) containing 0.005% Triton X-100. Upon addition of 0.01% hydrogen peroxide and 10 nM o-phenylenediamine (final concentrations) in Tris buffer, the increase in absorbance was monitored for one minute at 450 nm. The presence of eosonophils in the uterus was taken as an indication of estrogenic activity of a compound. The maximal velocity of a fifteen second interval was determined over the initial, linear portion of the reaction curve.

Although $EE_2$ caused a decrease in serum cholesterol when orally administered at 0.1 mg/kg/day, it also exerted a stimulatory action on the uterus so that $EE_2$ uterine weight was substantially greater than the uterine weight of untreated ovariectomized test animals. This uterine response to estrogen is well recognized in the art. Representative compounds of the present invention reduced serum cholesterol compared to the ovariectomized control animals. Moreover, relative to $EE_2$, representative compounds of the present invention have a diminished effect on uterine weight.

Compared to estrogenic compounds known in the art, the benefit of serum cholesterol reduction without as adverse of an affect on uterine weight is rare and desirable.

Relative to $EE_2$, which caused a substantial, expected increase in eosinophil infiltration, the representative compounds of the present invention had a significantly diminished effect on eosinophil infiltration.

In addition to the above demonstrated benefits of these representative compounds of the present invention, especially when compared to estradiol, the compounds tested were not estrogen mimetic.

MCF-7 Proliferation Assay

The affinity of a representative sample of the compounds of the present invention for the estrogen receptors was tested in a MCF-7 receptor proliferation assay. MCF-7 breast adenocarcinoma cells (ATCC HTB 22) were maintained in MEM (minimal essential medium, phenol red-free, Sigma Chemical Co., St. Louis, Mo.) supplemented with 10% fetal bovine serum (FBS) (v/v), L-glutamine (2 mM), sodium pyruvate (1 mM), HEPES [N-(2-hydroxyethyl) piperazine-N'-2-ethanesulfonic acid 10 mM], non-essential amino acids and bovine insulin (1 μg/mL) (maintenance medium). Ten days prior to assay, MCF-7 cells were switched to maintenance medium supplemented with 10% dextran-coated charcoal stripped fetal bovine serum (DCC-FBS) assay medium) in place of 10% FBS to deplete internal stores of steroids. MCF-7 cells were removed from maintenance flasks using cell dissociation medium ($Ca^{+2}/Mg^{+2}$ free HBSS (phenol red-free) supplemented with 10 mM HEPES and 2 mM EDTA). Cells were washed twice with assay medium and adjusted to 80,000 cells/mL. Approximately 100 μL (8,000 cells) were added to flat-bottom microculture wells (Costar 3596) and incubated at 37° C. in a 5% $CO_2$ humidified incubator for 48 hours to allow for cell adherence and equilibration after transfer. Serial dilutions of drugs or DMSO as a diluent control were prepared in assay medium and 50 μL transferred to triplicate microcultures followed by 50 μL assay medium for a final volume of 200 μL. After an additional 48 hours at 37° C. in a 5% $CO_2$ humidified incubator, microcultures were pulsed with tritiated thymidine (1 μCi/well) for four hours. Cultures were terminated by freezing at −70° C. for 4 hours followed by thawing and harvesting of microcultures using a Skatron Semiautomatic Cell Harvester. Samples were counted by liquid scintillation using a Wallac BetaPlace β-counter.

Relative to 17β-estradiol's known effects on the proliferation of MCF-7, the representative compounds of the present invention demonstrated significantly less stimulatory activity. In most cases an inhibitory effect was observed.

Bone Sparing: Five Week Ovariectomized Rat Model

General Preparation Procedure

Seventy-five day old female Sprague Dawley rats (weight range of 275 g–350 g) were obtained from Charles River Laboratories (Portage, Mich.). The animals were either bilaterally ovariectomized (OVX) or exposed to a Sham surgical procedure at Charles River Laboratories, and then shipped the day following surgery. Upon arrival, these rats were housed in metal hanging cases in groups of three or four animals per cage, and had ad libitum access to food (Teklad diet, TD 89222, 0.5% calcium, 0.4% phosphorous; Madison, Wis.) and water. Room temperature was maintained at 22.2° C.±1.7° C. with a minimum relative humidity of 40%. The photoperiod in the room was twelve hours light and twelve hours dark.

Dosing Regimen/Tissue Collection

Test compound preparation was the same as that described in the Estrogenicty assay above. After a one day acclimation period (two days post-OVX), dosing with test compounds was initiated. Oral gavages 20% CDX, representative compound of the invention (0.01 to 10 mg/kg), or 17α-ethynylestradiol (100 μg/kg) were delivered daily for 35 consecutive days. On the evening following the final dose, the animals were fasted. The next morning the animals were aneshetized with a mixture of Ketaset® and Rompun® (67 and 6.7 mg/kg respectively). The animals were asphyxiated with carbon dioxide and the left femur was removed from each animal, cleaned and frozen for subsequent X-ray evaluation.

Bone Assay

The distal end of the femur was X-rayed using a Norland NXR-1200 X-ray machine with a voltage of 47 kV and contrast at 4.5. Digitalized X-ray images were transferred to a computer station and image analysis of the X-ray scan was conducted. Quantitation was achieved by measuring the total number of pixels in a standard region of interest proximal to the growth plate, over a gray scale range of zero to 60.

When the above assay was run with the compound of Example 3 at a dose of 0.01 mg/kg, the X-ray evaluation resulted in 9.1% protection of the femur from bone loss.

For the majority of the methods of the present invention, compounds of formula I are administered continuously, from 1 to 3 times daily.

The specific dose of a compound administered according to this invention will, of course, be determined by the particular circumstances surrounding the case including, for example, the compound administered, the route of administration, the state of being of the patient, and the pathological condition being treated. A typical daily dose will contain a nontoxic dosage level of from about 5 mg to about 600 mg/day of a compound of the present invention. Preferred daily doses generally will be from about 15 mg to about 100 mg/day.

The compounds of this invention can be administered by a variety of routes including oral, rectal, transdermal, subucutaneus, intravenous, intramuscular, and intranasal, the selection of which will be decided by the attending physician. These compounds preferably are formulated prior to administration. Thus, another aspect of the present invention is a pharmaceutical formulation comprising an effective amount of a compound of formula I, or a pharmaceutical salt thereof, and a pharmaceutical carrier, diluent, or excipient. The total active ingredients in such formulations comprises from 0.1% to 99.9% by weight of the formulation.

Pharmaceutical formulations of the present invention can be prepared by procedures known in the art using well known and readily available ingredients. For example, the compounds of formula I can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinylpyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyline glycols.

The compounds also can be formulated as elixirs or solutions for convenient oral administration or as solutions appropriate for parenteral administration, for example, by intramuscular, subcutaneous, or intravenous routes. Additionally, the compounds are well suited for formulation as sustained-release dosage forms and the like. The formulations can be so constituted that they release the active ingredient only or preferably in a particular physiological location, possibly over a period of time. The coatings, envelopes, and protective matrices may be made, for example, from polymeric substances or waxes.

The following formulation examples are illustrative only and are not intended to limit the scope of the present invention. In the formulations which follow, "active ingredient" means a compound of formula I, or a salt thereof.

Hard gelatin capsules are prepared using the following:

Formulation 1
Gelatin Capsules

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The formulation above may be changed in compliance with the reasonable variations provided.

A tablet formulation is prepared using the ingredients below:

Formulation 2
Tablets

| Ingredient | Quantity (mg/tablet) |
| --- | --- |
| Active ingredient | 2.5–1000 |
| Cellulose, microcrystalline | 200–650 |
| Silicon dioxide, fumed | 10–650 |
| Stearate acid | 5–15 |

The components are blended and compressed to form tablets.

Alternatively, tablets each containing 2.5 mg–1000 mg of active ingredient are made up as follows:

Formulation 3
Tablets

| Ingredient | Quantity (mg/tablet) |
| --- | --- |
| Active ingredient | 25–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C.–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1 mg–1000 mg of medicament per 5 ml dose are made as follows:

| Formulation 4 Suspensions | |
|---|---|
| Ingredient | Quantity (mg/5 ml) |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

An aerosol solution is prepared containing the following ingredients:

| Formulation 5 Aerosol | |
|---|---|
| Ingredient | Quantity (% by weight) |
| Active ingredient | 0.25 |
| Ethanol | 25.75 |
| Propellant 22 (Chlorodifluoromethane) | 70.00 |

The active ingredient is mixed with ethanol and the mixture added to a portion of the propellant 22, cooled to 30° C., and transferred to a filling device. The required amount is then fed to a stainless steel container and diluted with the remaining propellant. The valve units are then fitted to the container.

Suppositories are prepared as follows:

| Formulation 6 Suppositories | |
|---|---|
| Ingredient | Quantity (mg/suppository) |
| Active ingredient | 250 |
| Saturated fatty acid glycerides | 2,000 |

The active ingredient is passed through a No. 60 mesh U.S. sieve and suspended in the saturated fatty acid glycerides previously melted using the minimal necessary heat. The mixture is then poured into a suppository mold of nominal 2 g capacity and allowed to cool.

An intravenous formulation is prepared as follows:

| Formulation 7 Intravenous Solution | |
|---|---|
| Ingredient | Quantity |
| Active ingredient | 50 mg |
| Isotonic saline | 1,000 mL |

The solution of the above ingredients is intravenously administered to a patient at a rate of about 1 mL per minute.

| Formulation 8 Combination Capsule I | |
|---|---|
| Ingredient | Quantity (mg/capsule) |
| Active ingredient | 50 |
| Premarin | 1 |
| Avicel pH 101 | 50 |
| Starch 1500 | 117.50 |
| Silicon Oil | 2 |
| Tween 80 | 0.5 |
| Cab-O-Sil | 0.25 |

| Formulation 9 Combination Capsule II | |
|---|---|
| Ingredient | Quantity (mg/capsule) |
| Active ingredient | 50 |
| Norethynodrel | 5 |
| Avicel pH 101 | 82.50 |
| Starch 1500 | 90 |
| Silicon Oil | 2 |
| Tween 80 | 0.50 |

| Formulation 10 Combination Tablet | |
|---|---|
| Ingredient | Quantity (mg/capsule) |
| Active ingredient | 50 |
| Premarin | 1 |
| Corn Starch NF | 50 |
| Povidone, K29-32 | 6 |
| Avicel pH 101 | 41.50 |
| Avicel pH 102 | 136.50 |
| Crospovidone XL10 | 2.50 |
| Magnesium Stearate | 0.50 |
| Cab-O-Sil | 0.50 |

We claim:

1. A compound of formula I:

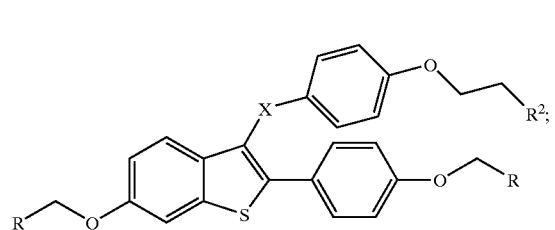

wherein:
R is independently at each occurrence NHC(O)$R^1$, O$R^1$, or S$R^1$;
$R^1$ is $C_1$–$C_6$ alkyl or aryl;
$R^2$ is pyrrolidin-1-yl, pipiperidin-1-yl, or hexamethyleneimin-1-yl; and
X is C=O, CH—OH, $CH_2$, O, or S; or a pharmaceutically acceptable salt or solvate thereof.

2. The compound according to claim 1 wherein X is C=O.

3. The compound according to claim 2 wherein $R^2$ is piperidin-1-yl.

4. The compound according to claim 3 wherein R is $OR^1$ and $R^1$ is $C_1$–$C_4$ alkyl.

5. The compound according to claim 4 wherein $R^1$ is methyl or ethyl.

6. The compound according to claim 3 wherein R is $NHC(O)R^1$ and $R^1$ is aryl.

7. The compound according to claim 2 which is the hydrochloride salt.

8. The compound according to claim 1 which is:

2-(4-[Methylthiomethoxy]phenyl)-3-(4-[(2-Piperidin-1-yl)ethoxy]benzoyl)-6-Methylthiomethoxybenzo[b]thiophene; 2-(4-[Phenylthiomethoxy]phenyl)-3-(4-[(2-Piperidin-1-yl)ethoxy]benzoyl)-6-Phenylthiomethoxybenzo[b]thiophene;

2-(4-[Ethoxymethoxy]phenyl)-3-(4-[(2-Piperidin-1-yl)ethoxy]benzoyl)-6-Ethoxymethoxybenzo[b]thiophene; 2-(4-[Methoxymethoxy]phenyl)-3-(4-[(2-Piperidin-1-yl)ethoxy]benzoyl)-6-Methoxymethoxybenzo[b]thiophene; or 2-(4-[Benzamidylmethoxy]phenyl)-3-(4-[(2-Piperidin-1-yl)ethoxy]benzoyl)-6-Benzamidylmethoxybenzo[b]thiophene; or a pharmaceutical salt or solvate thereof.

9. The compound according to claim 1 wherein X is O.

10. A pharmaceutical composition comprising an effective amount of a compound of claim 1 and a pharmaceutical carrier, diluent, or excipient.

11. The composition according to claim 10 wherein the compound of formula I is a compound wherein X is C=O.

12. A method for inhibiting osteoporosis which comprises administering to a woman in need of such inhibition an effective amount of a compound of claim 1, or a pharmaceutically acceptable salt or solvate thereof.

13. The method according to claim 12 wherein the compound of formula I is a compound wherein X is C=O.

14. A method for inhibiting hyperlipidemia which comprises administering to a woman in need of such inhibition an effective amount of a compound of claim 1, or a pharmaceutically acceptable salt or solvate thereof.

15. The method according to claim 14 wherein the compound of formula I is a compound wherein X is C=O.

16. A method for inhibiting estrogen-dependent cancer which comprises administering to a woman in need of such inhibition an effective amount of a compound of claim 1, or a pharmaceutically acceptable salt or solvate thereof.

17. The method according to claim 16 wherein the compound of formula I is a compound wherein X is C=O.

* * * * *